United States Patent
Smith et al.

(10) Patent No.: US 6,213,974 B1
(45) Date of Patent: *Apr. 10, 2001

(54) STEERABLE CATHETER HAVING SEGMENTED TIP AND ONE-PIECE INLET HOUSING, AND METHOD OF FABRICATING SAME

(75) Inventors: Gary A. Smith, Peachtree City; Mahase Nardeo; Robert C. Biggs, both of Alpharetta, all of GA (US)

(73) Assignee: Visionary Biomedical, Inc., Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/211,345

(22) Filed: Dec. 15, 1998

Related U.S. Application Data

(63) Continuation-in-part of application No. 09/126,863, filed on Jul. 31, 1998, which is a continuation-in-part of application No. 08/777,548, filed on Dec. 30, 1996, now Pat. No. 6,030,360.

(51) Int. Cl.[7] .................................................. A61M 37/00
(52) U.S. Cl. .................................. 604/95.01; 604/95.04; 604/528; 600/139; 600/146
(58) Field of Search ............................ 604/95.01, 95.04, 604/500, 508, 510, 513, 264, 523, 524, 525, 526, 528, 533, 539; 600/139, 146, 147, 149

(56) References Cited

U.S. PATENT DOCUMENTS

| | | | |
|---|---|---|---|
| D. 343,678 | 1/1994 | Snoke et al. | D24/112 |
| D. 349,340 | 8/1994 | Snoke et al. | D24/138 |
| 3,470,876 | 10/1969 | Barchilon | D24/138 |
| 3,525,561 | 8/1970 | Takahasi | D24/138 |
| 3,595,220 | 7/1971 | Kawahara | D24/138 |

(List continued on next page.)

FOREIGN PATENT DOCUMENTS

| | | |
|---|---|---|
| 1213571 | 3/1966 | (DE) . |
| 0343094 | 11/1989 | (EP) . |
| 3916288 A1 | 11/1989 | (DE) . |
| 0370158 | 5/1990 | (EP) . |
| 0489937A1 | 6/1992 | (EP) . |
| 990.417 | 9/1951 | (FR) . |
| WO88/00810 | 2/1988 | (WO) . |
| WO91/11213 | 8/1991 | (WO) . |
| WO94/01162 | 1/1994 | (WO) . |
| WO96/08993 | 3/1996 | (WO) . |

OTHER PUBLICATIONS

A Method For Epiduroscopy And Spinaloscopy, R. Blomberg, Acta Anaesthesiol Scand 1985, pp. 113–116.
Myeloscopy, International Orthopaedics, Yoshio Ooi et al., Springer–Verlag 1977, pp. 107–111.

(List continued on next page.)

*Primary Examiner*—Glenn K. Dawson
*Assistant Examiner*—Jennifer Maynard
(74) *Attorney, Agent, or Firm*—Gardner & Groff, P.C.

(57) ABSTRACT

A steerable catheter having a segmented tip formed from materials of differing hardnesses. A tip segment formed of softer material provides improved steerability, while an adjacent harder segment provides improved resistance against steering wire pull-through. Wear-resistant sleeves and a coined loop portion of steering wire provide additional resistance against steering wire pull-through. A tip fabrication method is also disclosed. The catheter includes a one-piece inlet housing with integral mounting fins for attachment to the catheter housing.

17 Claims, 5 Drawing Sheets

U.S. PATENT DOCUMENTS

| | | | |
|---|---|---|---|
| 3,605,725 | 9/1971 | Bentov | D24/138 |
| 3,892,228 | 7/1975 | Mitsui | 128/4 |
| 4,214,593 | 7/1980 | Imbruce et al. | 128/748 |
| 4,349,014 | 9/1982 | Takamatsu | 128/6 |
| 4,483,326 | 11/1984 | Yamaka et al. | 128/4 |
| 4,508,103 | 4/1985 | Calisi | 128/673 |
| 4,545,374 | 10/1985 | Jacobson | 128/303 R |
| 4,558,691 | 12/1985 | Okada | 128/6 |
| 4,573,448 | 3/1986 | Kambin | 128/1 R |
| 4,601,284 | 7/1986 | Arakawa et al. | 128/6 |
| 4,720,178 | 1/1988 | Nishioka et al. | 350/401 |
| 4,737,142 | 4/1988 | Heckele | 604/95 |
| 4,752,292 | 6/1988 | Lopez et al. | 604/244 |
| 4,776,844 | 10/1988 | Ueda | 604/95 |
| 4,796,615 | 1/1989 | Bullock et al. | 128/202.27 |
| 4,808,157 | 2/1989 | Coombs | 604/44 |
| 4,902,129 | 2/1990 | Siegmund et al. | 356/241 |
| 4,904,237 | 2/1990 | Janese | 604/28 |
| 4,905,666 | 3/1990 | Fukuda | 128/4 |
| 4,919,653 | 4/1990 | Martinez et al. | 604/117 |
| 4,930,521 | 6/1990 | Metzger et al. | 128/786 |
| 4,934,340 | 6/1990 | Ebling et al. | 128/6 |
| 4,965,319 | 10/1990 | Kawamoto | 525/194 |
| 4,968,298 | 11/1990 | Michelson | 604/36 |
| 4,973,312 | 11/1990 | Andrew | 604/158 |
| 4,983,165 | 1/1991 | Loiterman | 604/95 |
| 4,985,022 * | 1/1991 | Fearnot et al. | 604/282 |
| 4,986,262 | 1/1991 | Saito | 128/6 |
| 4,996,974 | 3/1991 | Ciarlei | 128/4 |
| 5,053,046 | 10/1991 | Janese | 606/215 |
| 5,084,043 | 1/1992 | Hertzman et al. | 606/3 |
| 5,085,631 | 2/1992 | Leighton | 604/28 |
| 5,108,364 | 4/1992 | Takezawa et al. | 604/43 |
| 5,131,382 | 7/1992 | Meyer | 128/6 |
| 5,143,475 | 9/1992 | Chikama | 403/291 |
| 5,167,221 | 12/1992 | Chikama | 128/4 |
| 5,168,864 | 12/1992 | Shockey | 128/4 |
| 5,188,594 | 2/1993 | Zilberstein | 604/51 |
| 5,195,541 | 3/1993 | Obenchain | 128/898 |
| 5,197,649 | 3/1993 | Bessler et al. | 227/179 |
| 5,198,301 | 3/1993 | Hager et al. | 428/355 |
| 5,199,950 | 4/1993 | Schmitt et al. | 604/95 |
| 5,215,105 | 6/1993 | Kizelshteyn et al. | 128/898 |
| 5,218,970 | 6/1993 | Turnbull et al. | 128/748 |
| 5,224,467 | 7/1993 | Oku | 128/4 |
| 5,226,879 | 7/1993 | Ensminger et al. | 604/93 |
| 5,232,442 | 8/1993 | Johnson et al. | 604/51 |
| 5,256,158 | 10/1993 | Tolkoff et al. | 604/280 |
| 5,284,489 | 2/1994 | Liu et al. | 606/228 |
| 5,289,831 | 3/1994 | Bosley | 128/899 |
| 5,298,571 | 3/1994 | Statz et al. | 525/330.2 |
| 5,308,324 | 5/1994 | Hammerslag et al. | 604/95 |
| 5,342,299 * | 8/1994 | Snoke et al. | 604/95 |
| 5,354,266 | 10/1994 | Snoke | 604/28 |
| 5,372,587 | 12/1994 | Hammerslag | 604/95 |
| 5,396,880 | 3/1995 | Kagan et al. | 128/6 |
| 5,397,840 | 3/1995 | Sullivan et al. | 525/221 |
| 5,399,164 | 3/1995 | Snoke et al. | 604/95 |
| 5,419,312 | 5/1995 | Arenberg et al. | 128/6 |
| 5,423,311 | 6/1995 | Snoke et al. | 128/6 |
| 5,431,168 * | 7/1995 | Webster, Jr. | 128/658 |
| 5,437,636 | 8/1995 | Snoke et al. | 604/95 |
| 5,454,794 | 10/1995 | Narciso et al. | 604/280 |
| 5,456,664 | 10/1995 | Heinzelmann et al. | 604/95 |
| 5,492,530 | 2/1996 | Fischell et al. | 604/49 |
| 5,496,269 | 3/1996 | Snoke | 604/28 |
| 5,507,732 | 4/1996 | McClure et al. | 604/280 |
| 5,516,847 | 5/1996 | Sullivan et al. | 525/221 |
| 5,526,820 | 6/1996 | Khoury | 128/748 |
| 5,545,149 | 8/1996 | Brin et al. | 604/265 |
| 5,549,580 | 8/1996 | Diaz | 604/280 |
| 5,556,381 | 9/1996 | Ensminger et al. | 604/93 |
| 5,569,221 | 10/1996 | Houser et al. | 604/282 |
| 5,638,819 | 6/1997 | Manwaring et al. | 128/653.1 |
| 5,658,263 | 8/1997 | Dang et al. | 604/280 |
| 5,662,622 | 9/1997 | Gore et al. | 604/282 |
| B1 4,919,112 | 12/1993 | Siegmund | 128/4 |

OTHER PUBLICATIONS

Eighteen–Guage Microscopic–Telescopic Needle Endoscope With Electrode Channel, Charles P. Olinger, M.D. and R.L. Ohlhaber, Surgical Neurology, vol. 2, 1974, pp. 151–160.

Myeloscopy: Intraspinal Endoscopy, J. Lawrence Pool, M.D., Surgery, Feb. 1942.

The Spinascope; A New Instrument For Visualizing The Spinal Canal And Its Contents, Ellas Lincoln Stern. Medical Record, pp. 31–32 (date unknown).

Percutaneous Evaluation of the Epidural and Subarachnoid Space with a Flexible Fiberscope, James E. Heavner, DVM, PhD, Regional Anesthesia 1991, p. 85.

Bjorn Holmstrom, Epiduroscopic Study of Risk of Catheter Migration Following Dural Puncture by Spinal and Epidural Needles—a Video Presentation, Regional Anesthesia, 1991.

Epidural Balloon Catheter System for Lysing Epidural Adhesion, Grigory Kizelshteyn, M.D., Regional Anesthesia 1991, p. 87.

The Lumbar Epidural Space in Patients Examined with Epiduroscopy, Rune G. Blomberg, MD and Sven S. Olsson, MD, Anesth. Analg. 1989, pp. 157–160.

The Dorsomedian Connectiive Tissue Band in the Lumbar Epidural Space of Humans: An Anatomical Study Using Epiduroscopy in Autopsy Cases, Rune Blomberg, MD, Anesth. Analg., 1986, pp. 747–752.

A Method For Epiduroscopy and Spinaloscopy: Presentation of Preliminary Results, R. Blomberg, Acta Anaesthesiol Scand 1985: 29: 113 to 116.

The Lumbar Epidural Space in Patients Examined with Epiduroscopy, R. Blomberg, Anesthesia and Analgesia, vol. 68, 1989, Supplement, pp. 157–160.

Direct Observation Of The Epidural Space With A Flexible Catheter–Secured Epiduroscopic Unit, G. Schutze and H. Kurtze, Journal of the American and European Societies of Regional Anesthesia (1994), pp. 85 to 89.

Catheter Replacement Of The Needle In Percutaneous Arteriography, A new technique by Sven Ivar Seldinger. Roentgen Diagnostic Dept. (ca. 1952).

Pain Management In The $21^{ST}$ Century: An Anesthesiologist's Look Into The Crystal Ball, Steven D. Waldman, MD Anesthesiology (1991).

Observation of Spinal Canal and Cisternae with the Newly Developed Small–Diameter, Flexible Fiberscopes Anesthesiology (date unknown).

ASRA News, Aug. 1995, pp. 1–13.

MedPRO Month, Dec. 1991, pp. 178–188.

* cited by examiner

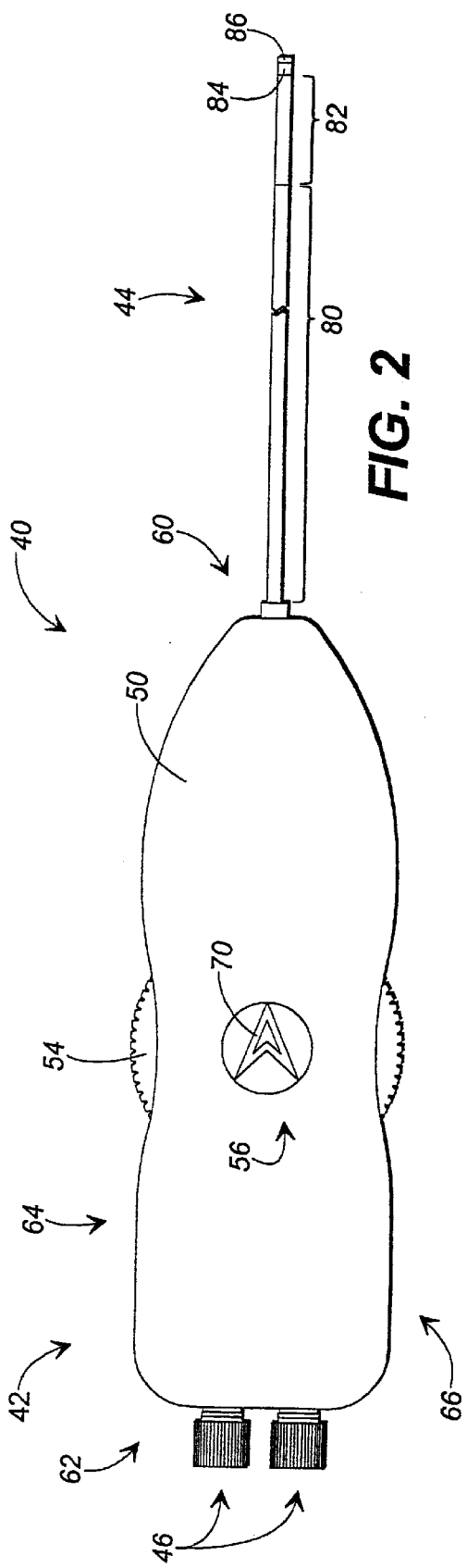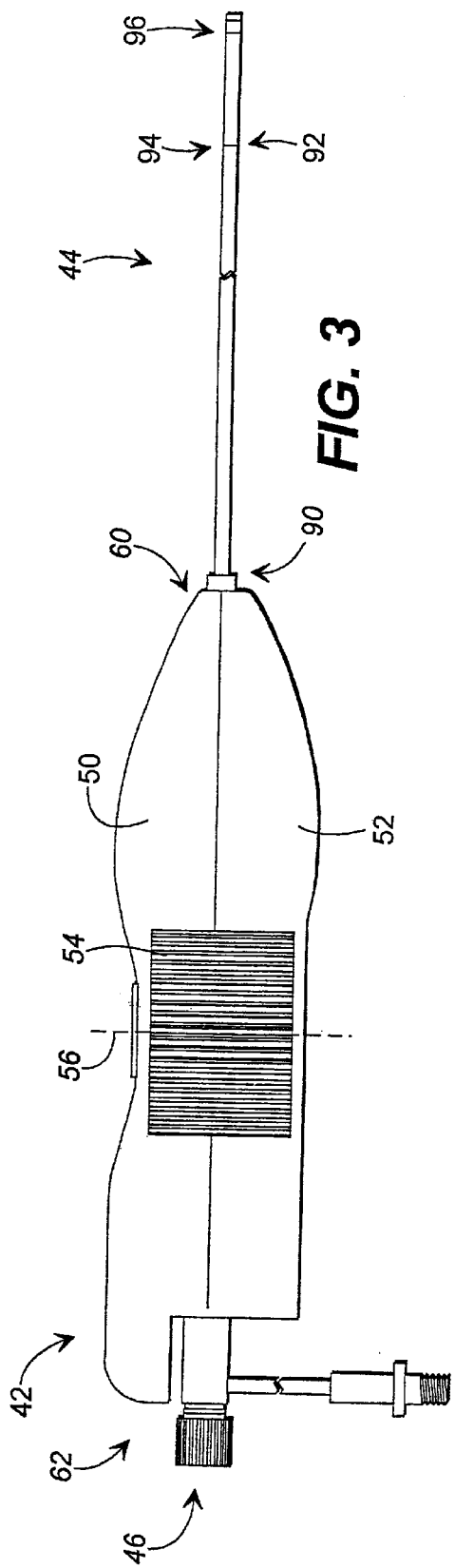

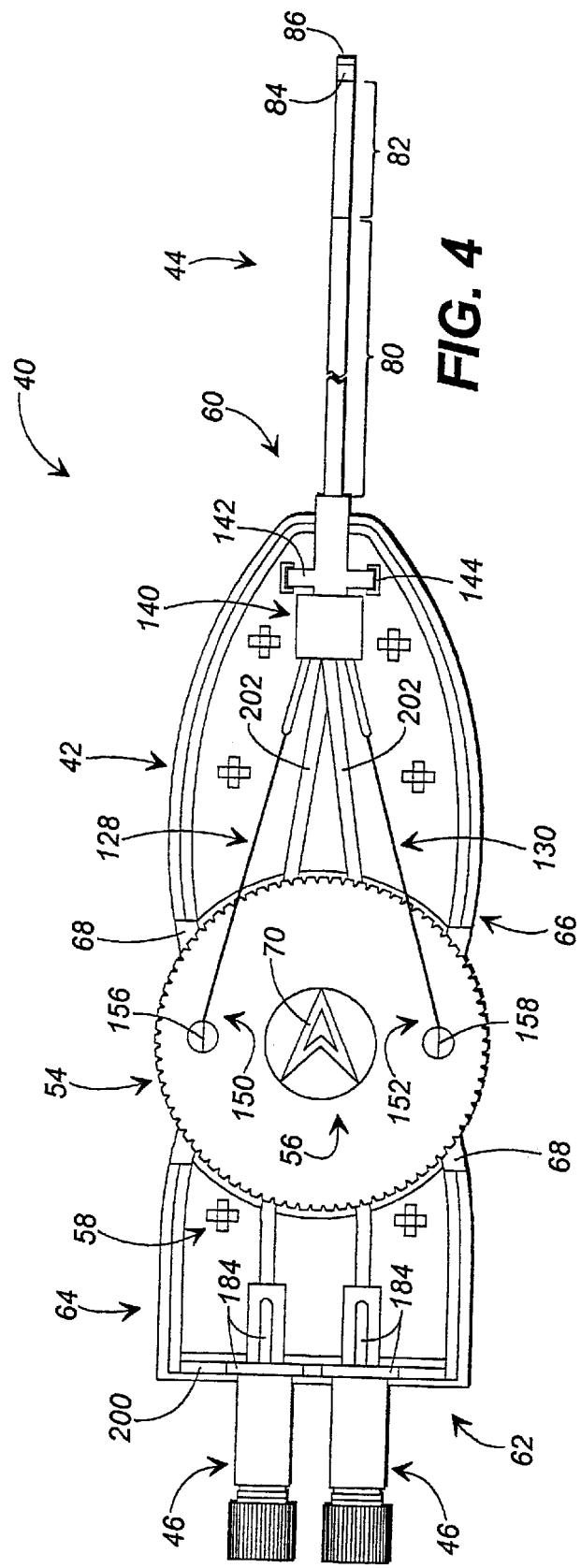

STEERABLE CATHETER HAVING SEGMENTED TIP AND ONE-PIECE INLET HOUSING, AND METHOD OF FABRICATING SAME

CROSS-REFERENCE TO RELATED APPLICATIONS

This application is a continuation-in-part and claims the benefit under 35 U.S.C. §120 of U.S. patent application Ser. No. 09/126,863, filed Jul. 31, 1998; which in turn was a continuation-in-part of U.S. patent application Ser. No. 08/777,548, filed Dec. 30, 1996, now U.S. Pat. No. 6,030,360, issued Feb. 29, 2000. The content of U.S. patent application Ser. Nos. 09/126,863 and 08/777,548 are incorporated herein by reference.

BACKGROUND OF THE INVENTION

1. Field of the Invention

The present invention relates generally to medical devices, and more particularly to a steerable catheter having a segmented tip configured for improved steerability, a tip assembly providing improved resistance to steering wire pull-through, and an improved one-piece inlet housing.

2. Description of Related Art

Medical practitioners frequently gain access to internal regions of a patient's body through the use of medical catheters in a variety of medical procedures, in order to reduce or eliminate the need for more invasive procedures. For example, medical catheters may be used to access internal body regions with a fiberoptic scope, light bundles, and/or other surgical instruments or devices, for a variety of diagnosis, treatment and/or material delivery purposes.

Steerable catheters have been developed to provide improved access to internal tissue. These catheters typically include a flexible catheter shaft and steering wires for controlling the flexure of the catheter shaft. A problem common to many previously existing steerable catheters is the retention of the steering wire or wires within the flexible material of the catheter shaft. The steering wire or wires typically comprise a small diameter length of high tensile strength material, whereas the flexible catheter shaft material typically must be relatively soft in order to provide sufficient flexibility. Thus, in many instances, the steering wire will cut through the flexible catheter shaft material, or will otherwise become disattached from the catheter shaft, rendering the catheter inoperable or compromising its utility. This problem is especially troublesome with small diameter catheters having one or more instrument access lumens therethrough, due to the reduced material thickness of the catheter.

Various approaches have been proposed for addressing the problem of steering wire detachment, a number of which are described in applicant's previous U.S. patent application Ser. Nos. 08/777,548 and 09/126,863, the content of which are incorporated herein by reference. Previously developed devices and methods have met with varying degrees of success, but none have proven fully successful for all applications.

An additional problem that has been found problematic in some previously known catheter designs results from the use of standard Touhy-Borst assemblies 10, as shown in FIG. 1, as the catheter inlet. The standard Touhy-Borst assembly 10 typically comprises a two-piece housing, having a first housing component 12 coupled to a second housing component 14 by means of a threaded luer 16 or other coupling. The use of this type of two-piece housing results in increased assembly time and expense, and presents a risk of detachment during use. Additionally, the coupling 16 permits relative rotational movement between the first housing component 12 and the second housing component 14. This is disadvantageous as it is has been found desirable to maintain the flush port 18 in a fixed position relative to the catheter housing. The standard Touhy-Borst assembly 10 is typically affixed to the catheter housing by means of mounting wings 20 provided on the second housing component 14. Even if the wings 20 are rigidly attached to second housing component 14, the rotational movement permitted at coupling 16 allows movement of the first housing component 12 and the flush port 18 thereof. In addition, the standard Touhy-Borst assembly 10 presents several steps or discontinuities 22a, 22b, 22c within its internal passage. These discontinuities present obstructions to instrument passage, and can result in abrasive wear and tear on sensitive instruments. The standard Touhy-Borst assembly 10 is also less than fully satisfactory for use as a catheter inlet housing, as it typically includes only two mounting wings 20. It has been found desirable to provide additional mounting wings angularly spaced about the circumference of the inlet housing for more accurate positioning. It has also been found desirable to increase the thickness and contact area of the mounting wings to provide more secure attachment to the catheter body housing.

Thus, it has been found that a need exists for an improved steerable catheter device, and for an improved catheter shaft, tip assembly, and inlet housing for catheters. It is to these and other needs that the present invention is primarily directed.

SUMMARY OF THE INVENTION

Briefly described, in preferred form, one aspect of the present invention provides a tip assembly for a steerable catheter, which assembly includes a catheter shaft having first and second steering wire lumens extending lengthwise therethrough. One or more access lumens may optionally be provided through the length of the catheter shaft, for permitting passage of a fiberoptic endoscope and other instruments, infused fluids, aspirated materials, and/or otherwise accessing internal regions. The tip assembly further includes a continuous length of steering wire having a first leg extending through the first steering wire lumen, a second leg extending through the second steering wire lumen, and a looped segment connecting the first and second legs. The looped segment of steering wire may optionally include a coined or otherwise formed expanded outer dimension. A first wear-resistant sleeve is preferably provided within the first steering wire lumen adjacent the looped segment of steering wire, and a second wear-resistant sleeve is preferably provided within the second steering wire lumen adjacent the looped segment of steering wire. The wear-resistant sleeves and coined portion of the steering wire provide improved resistance against steering wire pull-through or detachment from the soft material of the catheter shaft.

In another aspect, the present invention preferably comprises a segmented catheter shaft for a steerable catheter. The segmented catheter shaft preferably includes a first shaft segment having a rear distal end for connection to a catheter body housing, and a front distal end opposite the rear distal end. The segmented catheter shaft preferably further includes a tip segment having a first end fused to the front distal end of the first shaft segment, and a second end opposite the first end. The first shaft segment is preferably relatively stiff to prevent buckling of the catheter shaft, whereas the tip segment is relatively flexible, as compared to the first shaft segment, for improved steerability. The segmented catheter shaft preferably further includes an end segment having a first end fused to the second end of the tip segment, and a second end opposite the first end. In preferred form, the segmented catheter shaft also includes first and second steering wire lumens extending lengthwise through the first shaft segment, the tip segment, and the end segment; and optionally includes one or more access lumens extending throughout the length of the catheter shaft. A continuous length of steering wire is preferably provided, having a first leg extending through the first steering wire lumen and a second leg extending through the second steering wire lumen. A looped segment of the length of steering wire connects the first and second legs, extending across the second end of the end segment of the catheter shaft. A cover segment is preferably also provided, overlying at least a portion of the second end of the end segment, and encapsulating the looped segment of steering wire between the second end of the end segment and the cover segment. The end segment and cover segment are preferably formed of relatively stiff materials of construction, as compared to the tip segment, to resist steering wire pull-through. Wear-resistant sleeves can be provided in the steering wire lumens of the end segment to provide improved resistance to steering wire pull-through.

Another aspect of the present invention provides a method of forming a segmented catheter shaft. The method preferably comprises providing a first shaft segment, a tip segment, and an end segment, each having first and second steering wire lumens extending lengthwise therethrough. One or more access lumens can optionally also be provided through the first shaft segment, the tip segment, and the end segment. Mandrels are inserted through the steering wire lumens and, if provided, the access lumens. The tip segment is arranged on the mandrels between the first shaft segment and the end segment. The first shaft segment, tip segment and end segment are then bonded end-to-end, to form a shaft assembly having a connecting end comprising a portion of the first shaft segment and a free end comprising a portion of the end segment. The mandrels are removed, and a continuous length of steering wire is inserted through the shaft assembly, the steering wire having a first leg extending through the first steering wire lumen, a second leg extending through the second steering wire lumen, and a looped segment connecting the first and second legs adjacent the tip end of the shaft assembly. The looped segment of steering wire is then encapsulated between the free end of the shaft assembly and a cover segment applied to overlie at least a portion of the free end of the shaft assembly. In a further preferred embodiment, the looped segment of the steering wire is provided with an expanded outer dimension larger than an inner dimension of the first and second steering wire lumens, and/or wear-resistant sleeves can be installed in the steering wire lumens of the end segment prior to installing the steering wire. The first shaft segment and the end segment are preferably formed from a material having a first stiffness, and the tip segment from a material having a second stiffness less than the first stiffness. In a further preferred embodiment, a manifold is formed at the connecting end of the shaft assembly by inserting core pins into the steering wire lumens and, if provided, into the access lumen(s), and injection molding the manifold around the core pins. The core pins are then removed from the lumens upon demolding of the manifold.

Another aspect of the present invention provides an inlet housing for a catheter. The inlet housing preferably includes a unitary body portion having an instrument inlet, an outlet, an internal passage extending between the instrument inlet and the outlet, and an outer mounting surface. A sealing element is preferably provided adjacent the instrument inlet. In a further preferred embodiment, the inlet housing includes a flush port in fluid communication with the internal passage. One or more mounting flanges can be provided, extending outwardly from the unitary body portion. In a preferred embodiment, four mounting flanges are provided, spaced circumferentially about the unitary body portion at 90° intervals, with one of the mounting flanges generally aligned with the flush port. The internal passage of the inlet housing preferably provides a smooth transition between the instrument inlet and the outlet, whereby tools, instruments or other materials inserted therethrough will not meet with substantial obstruction.

A further aspect of the present invention provides a steerable catheter incorporating one or more of the above-described features. In a preferred form, the steerable catheter includes a catheter body having a steering actuator for steering an attached catheter shaft. The steerable catheter shaft preferably is formed from segments of different stiffnesses as described above, and includes first and second steering wire lumens and at least one access lumen extending lengthwise therethrough. The steerable catheter preferably includes a tip assembly comprising a continuous length of steering wire having a first leg extending through the first steering wire lumen, a second leg extending through the second steering wire lumen, and a looped segment connecting the first and second legs of the steering wire. The ends of the first and second legs opposite the looped segment are coupled to the steering actuator. Wear-resistant sleeves are preferably provided within the first and second steering wire lumens adjacent the looped segment of the steering wire. One or more inlet housings are preferably mounted to the catheter body housing, one inlet housing corresponding to each of the access lumens provided through the segmented catheter shaft. One or more access conduits are preferably also provided, coupling each inlet housing to its corresponding access lumen.

These and other features and advantages of preferred forms of the present invention are described herein with reference to the drawing figures.

BRIEF DESCRIPTION OF THE DRAWING FIGURES

FIG. 2 shows a top view of a steerable catheter according to a preferred form of the present invention.

FIG. 3 shows a side view of the steerable catheter shown in FIG. 2.

FIG. 4 shows a top view of a portion of the steerable catheter shown in FIG. 2, with the top cover removed to show internal components.

DETAILED DESCRIPTION

Figure 13:
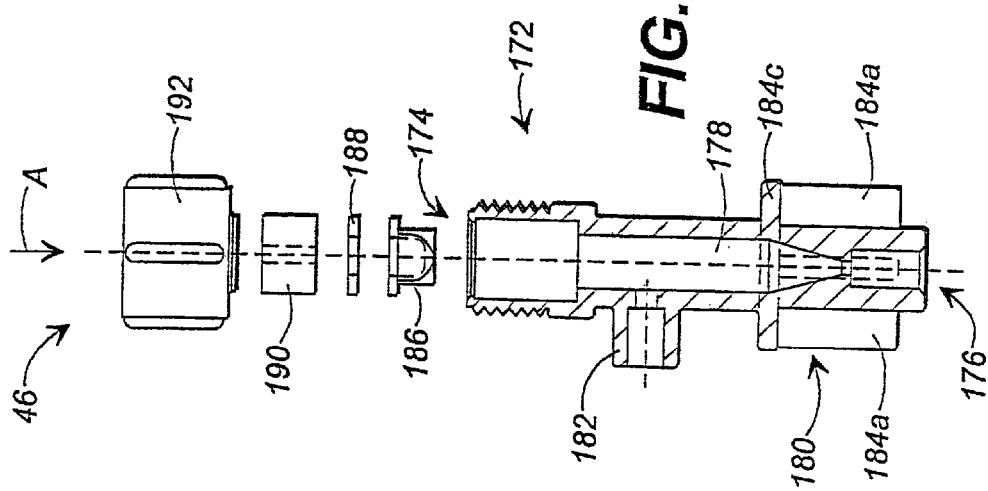
FIG. 13 shows a side view, in partial cross-section, of an inlet housing according to a preferred form of the present invention.
Figure 1:
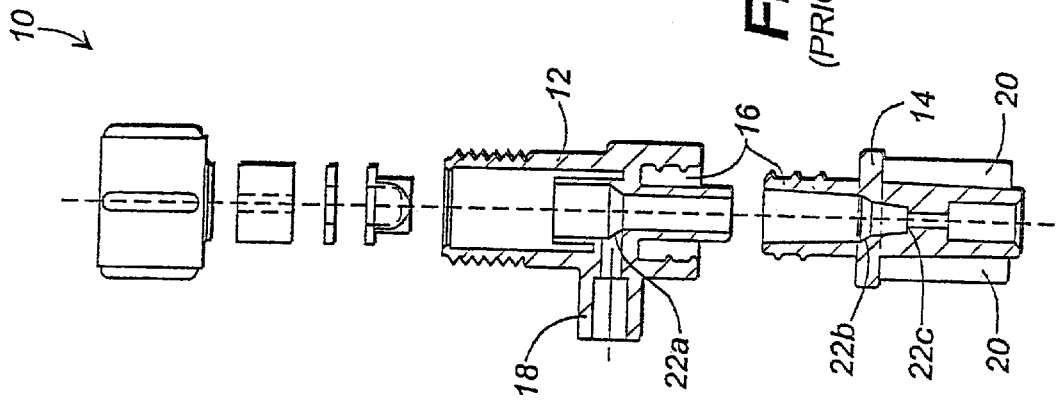
FIG. 1 shows a side view, in partial cross-section of a prior art Touhy-Borst assembly.

Referring now to the drawing figures, wherein like reference numerals represent like parts throughout, preferred forms of the present invention will now be described. As seen best with reference to FIGS. 2–5, the present invention generally comprises a steerable catheter 40, having a catheter body 42, a segmented catheter shaft 44, and at least one inlet housing 46. In a preferred form, the catheter body 42 comprises an upper housing shell 50 and a lower housing shell 52. A steering actuator such as, for example, a rotatably mounted dial 54 is preferably mounted in or on the catheter body 42. In the depicted embodiment, the dial 54 is rotatable about an axis 56 formed by cooperating projections and recesses on and in the dial 54 and one or both of the housing shells 50, 52. The dial 54 is preferably retained in place between the housing shells 50, 52, which are attached to one another in their assembled configuration by adhesive, thermal welding, and/or one or more couplings 58, such as cooperating pins and holes, resilient couplings, screws, rivets or other fasteners. The catheter body 42 generally comprises a forward end 60, a rear end 62, and first and second sides 64, 66, and is generally sized and shaped to be comfortably manipulated by a practitioner's hand. The catheter body is preferably fabricated from plastic or another substantially rigid material of construction. One or more cutout sections 68 can be provided in one or both of the housing shells 50, 52 to provide clearance for the steering actuator. The housing shells 50, 52 can also be provided with engagement features and openings, as required for mounting of the inlet housings 46 and the catheter shaft 44, as is more fully discussed below. The steering actuator can additionally comprise directional indicating means 70 for visually indicating the deflection of the steering actuator, and thereby the expected degree of displacement of the steerable tip of the catheter shaft 44.

The segmented catheter shaft 44 of the present invention will be described with particular reference to FIGS. 2–10. In a preferred embodiment depicted in the figures, the catheter shaft 44 generally comprises a first shaft segment 80, a tip segment 82, an end segment 84, and a cover segment 86. The first shaft segment 80 comprises a rear distal end 90 for connection to the forward end 60 of the catheter body 42, and a front distal end 92 generally opposite said rear distal end 90. The tip segment 82 preferably comprises a first end 94 fused or otherwise attached to the front distal end 92 of the first shaft segment 80, and a second end 96 generally opposite the first end 94. The end segment 84 preferably comprises a first end 98 fused or otherwise attached to the second end 96 of the tip segment 82 and a second end 100 generally opposite the first end 98. The cover segment 86 preferably overlies at least a portion of the second end 100 of the end segment 84.

In preferred form, the first shaft segment 80 is formed from a material having a first stiffness and the tip segment 82 is formed from a material having a second stiffness less than the first stiffness. In this manner, the first shaft segment 80 resists buckling along its length, and the relatively softer, more flexible tip segment 82 permits improved steerability. In a presently preferred example embodiment, the first shaft segment 80 is formed from a 7233 durometer PeBax (plastic) extrusion having a diameter of approximately 0.118 inch, and the tip segment 82 is formed from a 4033 durometer PeBax extrusion of substantially identical cross-section and diameter. The end segment 84 is preferably formed from a material having a third stiffness greater than the second stiffness, for example, a 7233 durometer PeBax extrusion substantially identical to that of the first shaft segment 80. The provision of the end segment 84 having substantially greater hardness than the tip segment 82 provides increased resistance to steering wire detachment during operation. The cover segment 86 is preferably formed from a relatively hard material such as 7233 durometer PeBax, but can alternatively be formed from a softer material such as 4033 durometer PeBax. The lengths of the segments of the catheter shaft 44 will vary depending upon the intended application. In a presently preferred example embodiment, the first shaft segment 80 is between 10" to 14", and most preferably approximately 11" in length; the tip segment 82 is approximately 1.5" in length; the end segment 84 is approximately 0.200" to 0.500" in length; and the cover sement 86 is approximately 0.200" or less in length. The segments of the catheter shaft 44 are thermal welded or otherwise fused to one another end-to-end, with any internal lumens aligned between the segments, to form a shaft assembly 104 having a connecting end 106 comprising the rear distal end 90 of the first shaft segment 80, and a free end 108 comprising the end segment 84 and cover segment 86.

As seen best with reference to FIGS. 6–12, the catheter shaft 44 preferably comprises first and second steering wire lumens 112, 114 extending lengthwise through the first shaft segment 80, the tip segment 82, and the end segment 84. The diameter of the steering wire lumens 112, 114 may vary depending upon the intended application. In a presently preferred embodiment, the diameter of the steering wire lumens 112, 114 is approximately 0.014 inch. The catheter shaft 44 preferably has a generally round cross-section, as seen best with reference to FIGS. 7 and 11. The steering wire lumens 112, 114 are arranged generally diametrically opposite one another along a first diameter of the cross-section. In a further preferred embodiment, the catheter shaft 44 optionally further comprises one or more (two are shown) access lumens 116, 118 for allowing passage of instruments such as a fiberoptic endoscope or surgical implements, and/or for infusion and aspiration of fluids or other materials. The diameter of the access lumens 116, 118 may vary depending upon the intended application. In a presently preferred embodiment, the diameter of the access lumens 116, 118 is approximately 0.051 inch. The access lumens 116, 118 are preferably arranged generally diametrically opposite one another along a second diameter generally perpendicular to the first diameter.

The catheter shaft 44 preferably further comprises a tip assembly 120, which will be described with particular reference to FIGS. 6–12. The tip assembly 120 preferably comprises a first wear resistant sleeve 122 disposed at least in part within the first steering wire lumen 112 of the end segment 84, and a second wear resistant sleeve 124 disposed at least in part within the second steering wire lumen 114 of the end segment 84. The wear resistant sleeves are preferably formed from stainless steel, other metals, ceramics or other materials having a high hardness and resistance to wear. A continuous length of steering wire 126 is provided, having a first leg 128 extending through the first steering wire lumen 112, and a second leg 130 extending through the second steering wire lumen 114. In preferred form, the steering wire 126 comprises a 0.010 diameter wire. A looped segment 132 of the length of steering wire 126 extends between the first leg 128 and the second leg 130. The first leg 128 of the steering wire 126 extends through the first wear resistant sleeve 122, and the second leg 130 extends through the second wear resistant sleeve 124. In this manner, as tension is applied to the steering wire 126 during operation, the wear-resistant sleeves 122, 124 prevent the wire 126 from cutting or otherwise damaging the softer plastic material of the catheter shaft 44. In addition, the relatively harder material of construction of the end segment 84 provides improved holding of the sleeves 122, 124, and improved resistance to damage from the steering wire 126 than would be provided by the relatively softer material of the tip segment 82.

Figure 9:
FIG. 9 shows an end view, from line 9—9 in FIG. 8, of the steering wire.
Figure 6:
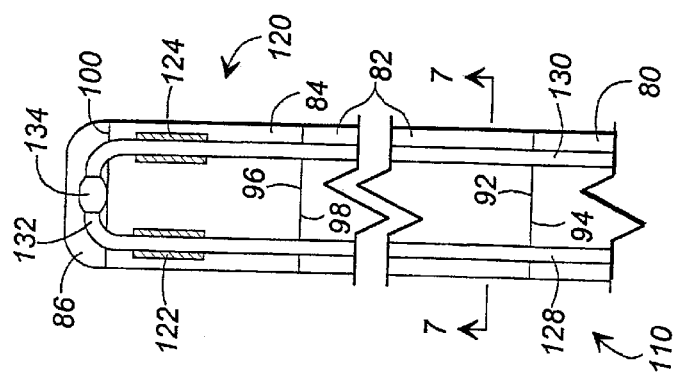
FIG. 6 shows a plan view of a tip assembly of a steerable catheter, in partial cut-away view, according to one form of the present invention.

In the embodiment of the present invention depicted in FIGS. 6–9, at least a portion of the looped segment 132 of the steering wire 126 is provided with an expanded outer dimension 134. The expanded portion 134 is larger in at least one dimension than the inside diameter of the opening through the wear-resistant sleeves 122, 124, so that the sleeves 122, 124 and the expanded portion 134 of the steering wire 126 cooperate to resist steering wire pull-through. In a preferred embodiment, the expanded portion 134 of the steering wire 126 is a coined portion formed by crimping to deform the wire 126. The expanded outer dimension 134 is preferably in the direction of the plane of the steering wire 126, as seen best with reference to FIG. 8. In this manner, the thickness of the expanded portion, when viewed end-on as shown in FIG. 9, is reduced, thereby reducing or eliminating any potential interference by the steering wire 126 with the openings of the access lumens 116, 118. In a preferred embodiment, the entire looped segment 132 of the steering wire 126, between the first wear-resistant sleeve 122 and the second wear-resistant sleeve 124, is coined to have an expanded outer dimension in the plane of the steering wire 126. In an alternate embodiment shown in FIGS. 10–12, the looped segment 132 of the steering wire 126 is not provided with an expanded outer dimension. Encapsulation of the looped segment 132 of the steering wire 126 between the end segment 84 and the cover segment 86 further affixes the steering wire 126 in place, providing additional resistance to steering wire pull-through.

Figure 5:
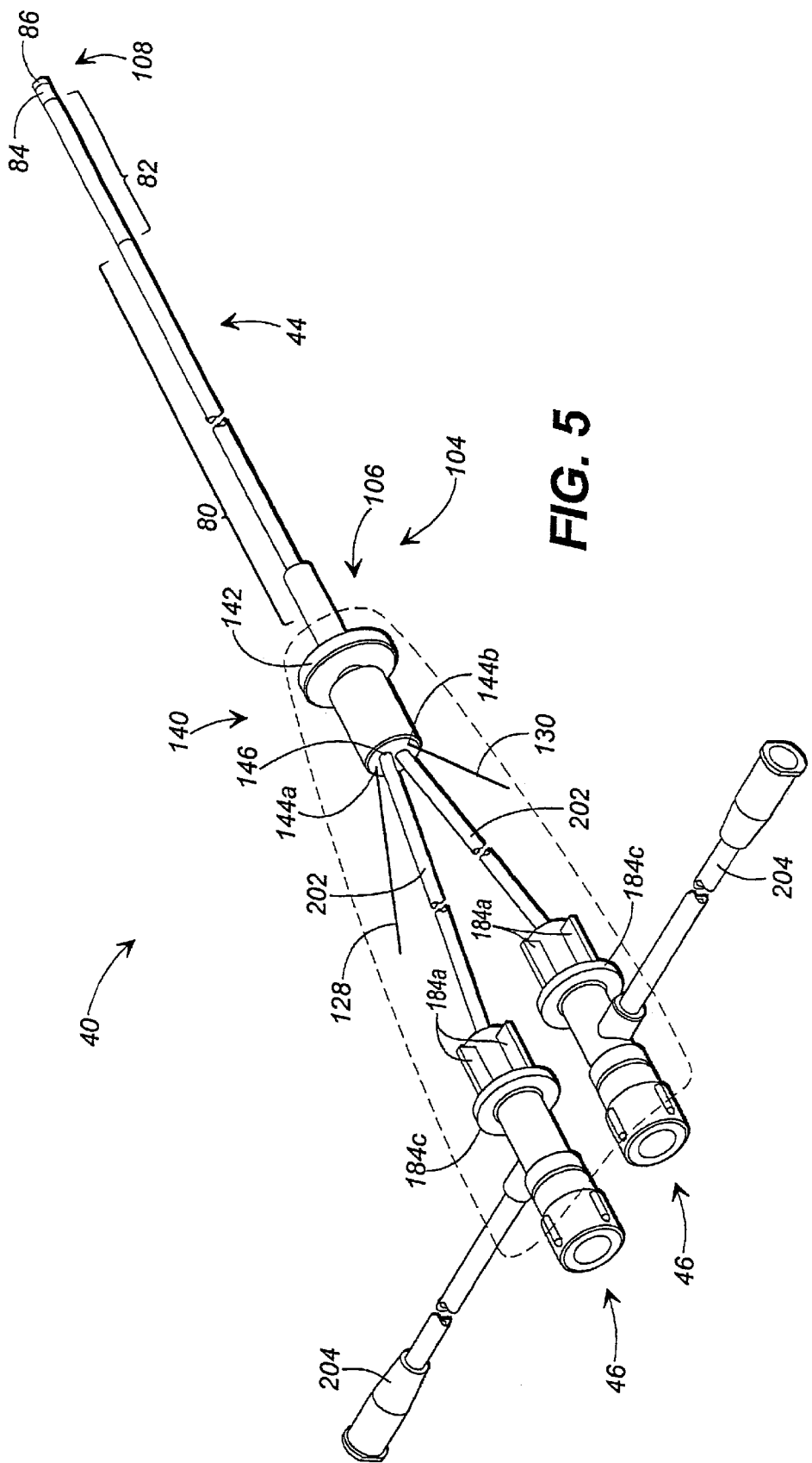
FIG. 5 shows a detailed view of certain internal components of the steerable catheter shown in FIG. 2, with the housing removed for clarity and shown generally in phantom lines.
Figure 11:
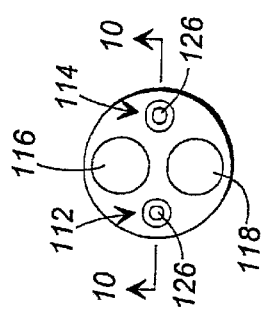
FIG. 11 shows a cross-sectional view, taken at line 11—11 of FIG. 10, of the tip assembly shown in FIG. 10.
Figure 12:
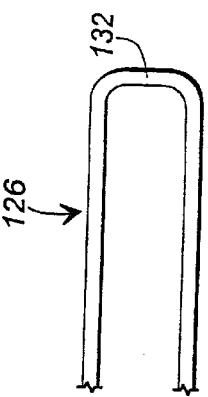
FIG. 12 shows a plan view of a steering wire portion of the tip assembly shown in FIG. 10.
Figure 10:
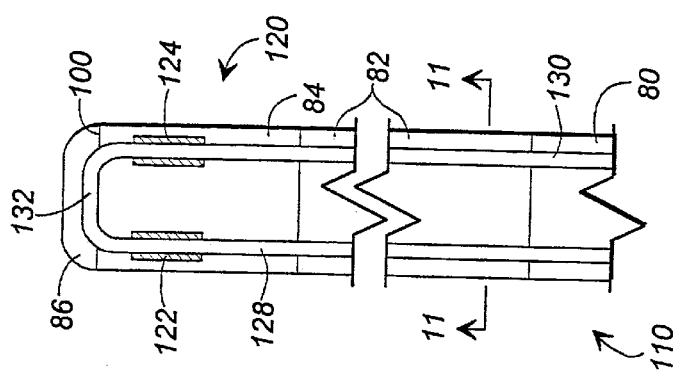
FIG. 10 shows a plan view of a tip assembly of a steerable catheter, in partial cut-away view, according to another form of the present invention.
Figure 7:
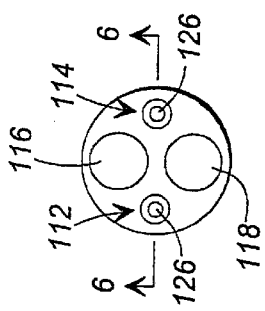
FIG. 7 shows a cross-sectional view, taken at line 7—7 of FIG. 6, of the tip assembly shown in FIG. 6.
Figure 8:
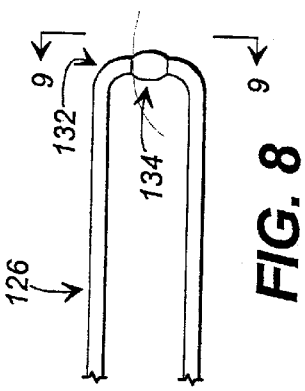
FIG. 8 shows a plan view of a steering wire portion of the tip assembly shown in FIG. 6.

In preferred form, the catheter shaft 44 further comprises a manifold 140, as shown in FIGS. 4 and 5. The manifold 140 is coupled to the rear distal end 90 of the first shaft segment 80. Mounting means, such as a radially projecting flange 142, are preferably provided on the outer surface of the manifold 140 for attaching the catheter shaft 44 to the catheter body housing 42. For example, in the depicted embodiment, the flange 142 is adhesively secured within cooperating channel elements 144 provided within the upper and lower housing shells 50, 52 adjacent the forward end 60. The manifold 140 preferably further comprises one or more steering wire passages 144 extending therethrough, and communicating with the steering wire lumens 112, 114 of the shaft assembly 104. The manifold 140 preferably further comprises one or more access passages 146 extending therethrough, and communicating with the access lumens 116, 118 of the shaft assembly 104.

As seen best with reference to FIG. 4, a first free end 150 of the first leg 128 of the steering wire 126 is attached to a first connection point of the steering actuator, and a second free end 152 of the second leg 130 of the steering wire 126 is attached to a second connection point of steering actuator. For example, in the depicted embodiment, the first and second connection points of the steering actuator comprise slotted posts 156, 158 projecting from the steering dial 54. The free ends 150, 152 are inserted into the slots, and secured therein with hot melt or other adhesive. The slotted posts 156, 158 are preferably mounted generally diametrically opposite one another on the dial 54. The steering wire 126 thus extends continuously from the first free end 150 attached to the dial 54, through a first steering wire passage 144a of the manifold 140, through the first steering wire lumen 112 of the shaft assembly 104, through the first wear-resistant sleeve 122, to the looped segment 132 adjacent the free end 108, and loops back through the second wear-resistant sleeve 124, through the second steering wire lumen 114 of the shaft assembly 104, through a second steering wire passage 144b of the manifold 140, to the second free end 152 attached to the dial 54 generally opposite the first free end 150. So arranged, rotation of the steering dial 54 about axis 56 in a first rotational direction causes displacement of the free end 108 of the shaft assembly in a first direction, and rotation of the steering dial 54 about axis 56 in a second rotational direction opposite the first direction causes displacement of the free end 108 of the shaft assembly in a second direction opposite the first direction.

The present invention preferably further provides an improved inlet housing 46. As seen best with reference to FIG. 13, the inlet housing 46 preferably comprises a unitary body portion 172 having an instrument inlet 174, an outlet 176, an internal passage 178 extending between the instrument inlet 174 and the outlet 176, and an outer mounting surface 180. The unitary body portion 172 preferably comprises a flush port 182 in fluid communication with the internal passage 178, for allowing passage of fluids such as, for example, saline fluid, pharmaceuticals, anesthetics, biologically active materials, markers, or other materials. As depicted, the flush port 182 extends outwardly from the exterior surface of the inlet housing 46, generally perpendicular to the direction of the internal passage 178, to form a generally T-shaped component. The flush port 182 can alternatively extend outwardly at an angle to form a generally Y-shaped component. A check valve, flow restricting orifice, and/or other flow control devices (unshown) can optionally be provided in the flush port 182.

The outer mounting surface 180 of the inlet housing 46 preferably comprises one or more mounting flanges 184 extending outwardly from the unitary body portion, for attaching the inlet housing 46 to an external structure or device such as, for example, the catheter body 42 described above. In the embodiment depicted in the figures, a circumferential mounting flange 184c, and a plurality of axial mounting flanges 184a, are provided. In preferred form, four axial mounting flanges 184a are provided, spaced circumferentially about the unitary body portion at approximately 90° intervals. One of the axial mounting flanges 184a is preferably generally aligned with the flush port 182, thereby enabling attachment of the inlet housing 46 to an external structure with the flush port 182 aligned generally parallel to or generally perpendicular to a mounting component of the external structure. Because the unitary body portion 172 of the inlet housing 46 of the present invention comprises a single component formed of a substantially rigid material, the flush port 182 and the mounting flanges 184 are substantially fixed in position relative to one another. In this manner, the inlet housing 46 of the present invention eliminates certain disadvantages found to result from the rotational movement permitted between the housing components of prior art Touhy-Borst fittings joined by threaded connections.

The inlet housing 46 preferably further comprises a sealing element within the internal passage, for example, adjacent the instrument inlet 174. In preferred form, the sealing element comprises a check valve such as an elastomeric duck-bill valve 186. The duck-bill valve 186 can be retained in place within the internal passage by means of a washer 188, a bushing 190, and a retaining cap 192 capable of attachment to the unitary body portion 172 such as by a threaded coupling.

The internal passage 178 of the inlet housing 46 preferably comprises a generally smooth transition throughout its entire length, from the instrument inlet 174 to the outlet 176. As used herein, "generally smooth transition" is intended to mean that the passage 178 presents no reductions in internal dimension, in the direction A of instrument insertion, at an angle greater than approximately 30° measured relative to an immediately adjacent wall surface of the internal passage.

The steerable catheter 40 of the present invention preferably comprises at least one inlet housing 46. For example, and with reference to FIGS. 2–5, two inlet housings 46 are preferably mounted within the catheter body 42 adjacent the rear end 62, with their instrument inlets 174 and flush ports 182 externally accessible. One inlet housing 46 is preferably provided for each access lumen 116, 118 in the shaft assembly 104. Engaging recesses 200 are preferably provided in the upper and lower housing shells 50, 52 to receive mounting flanges 184. The cooperating flanges 184 are attached within the recesses 200, preferably by adhesive, compression fit, thermal welding or other attachment means, thereby rigidly fixing the position of the inlet housings 46 and, if provided, the flush ports 182 thereof, relative to the catheter body 42. An access conduit such as a proximal extension 202 extends between each inlet housing and a corresponding access passage 146 in the manifold 140, providing communication and passage of instruments, fluids and other objects and materials between the internal passage 178 of each inlet housing 46 and the corresponding access lumen 116, 118 of the shaft assembly 104. In addition, a side extension 204 can be provided extending from each flush port 182, for connection to an external fluid source. In preferred form, the proximal extensions 202 and the side extensions 204 are preferably formed from a smooth-walled, flexible plastic tubing.

The present invention further comprises a method of forming a segmented catheter shaft, the shaft being substantially similar to the segmented catheter shaft 44 described above. A first shaft segment, a tip segment, and an end segment are provided, each having first and second steering wire lumens extending lengthwise therethrough. The first shaft segment, the tip segment, and the end segment preferably further comprise at least one access lumen extending lengthwise therethrough. The first shaft segment is preferably formed from a material having a first stiffness. In a presently preferred embodiment, the first shaft segment is formed from a 7233 durometer PeBax extrusion. The tip segment is preferably formed from a material having a second stiffness less than said first stiffness. In the presently preferred embodiment, the tip segment is formed from a 4033 durometer PeBax extrusion. The end segment is preferably formed from a material having a stiffness greater than that of the tip segment. In the presently preferred embodiment, the first shaft segment is formed from a 7233 durometer PeBax extrusion.

The first shaft segment, the tip segment, and the end segment are then bonded end-to-end, with the tip segment arranged between the first shaft segment and the end segment, to form a shaft assembly having a connecting end comprising a portion of the first shaft segment and a free end comprising a portion of the end segment. In order to prevent the internal lumens of the shaft segments from collapsing during the bonding process, mandrels are preferably inserted through the first and second steering wire lumens, and if present the access lumens, of the first shaft segment, the tip segment, and the end segment. The mandrels can comprise, for example, stainless steel rods and/or wires approximately matching the internal diameters of the lumens. According to the preferred method, the several segments of the shaft assembly are then bonded by thermal welding. The mandrels are then removed.

Optionally, a manifold can then be formed at the connecting end of the shaft assembly. The manifold is preferably formed by inserting core pins into the steering wire lumens and the access lumens at the connecting end of the shaft assembly, and injection molding plastic into a mold around the core pins to form the manifold. The core pins are then removed upon formation of the manifold. The openings remaining in the manifold after removal of the core pins form the steering wire passages and access passages through the manifold.

A continuous length of steering wire is then inserted through the steering wire lumens. Optionally, a first wear-resistant sleeve can be installed within the first steering wire lumen of the end segment, and a second wear-resistant sleeve installed within the second steering wire lumen of the end segment prior to insertion of the steering wire into the steering wire lumens. A first leg of the steering wire is inserted to extend through the first steering wire lumen, and a second leg of the steering wire is inserted to extend through the second steering wire lumen. A looped segment connects the first and second legs adjacent the tip end of the shaft assembly. The method of the present invention can optionally further comprise providing a portion of the looped segment of the steering wire with an expanded outer dimension larger than an inner dimension of the steering wire lumens, for example, by coining.

According to the preferred method, the looped segment of the steering wire is preferably encapsulated within a cover segment overlying at least a portion of the tip end of the shaft assembly. Mandrels or pins are inserted into the tip ends of the access lumens to prevent the formation of obstructions therein during the encapsulation process. A short cover segment of plastic, such as a 4033 or 7233 durometer PeBax extrusion is mounted over the pins or mandrels, and thermal welded to the tip end of the shaft assembly. The thermal welding process encapsulates the looped segment of steering wire between the end segment and the cover segment. The pins or mandrels are then removed.

While the invention has been described in its preferred forms, it will be readily apparent to those of ordinary skill in the art that many additions, modifications and deletions can be made thereto without departing from the spirit and scope of the invention.

What is claimed is:

1. A tip assembly for a catheter shaft of a steerable catheter, the catheter shaft having first and second steering wire lumens extending lengthwise therethrough, said tip assembly comprising:
   (a) a length of steering wire having a first leg extending through said first steering wire lumen, a second leg extending through said second steering wire lumen, and a looped segment connecting said first and second legs;
   (b) a first wear-resistant sleeve within said first steering wire lumen adjacent said looped segment of said steering wire, said first wear-resistant sleeve defining an opening therethrough for passage of said first leg of steering wire; and
   (c) a second wear-resistant sleeve within said second steering wire lumen adjacent said looped segment of said steering wire, said second wear-resistant sleeve defining an opening therethrough for passage of said second leg of steering wire;
   wherein said looped segment of said steering wire comprises a coined portion having an expanded outer dimension larger than said openings through said first and second wear-resistant sleeves.

2. A steerable catheter comprising:
   (a) a catheter body housing comprising a steering actuator;
   (b) a segmented catheter shaft mounted to said catheter body housing and having first and second steering wire lumens and at least one access lumen extending lengthwise therethrough, said catheter shaft having a tip assembly comprising:
      (i) a length of steering wire having a first leg extending through said first steering wire lumen, a second leg extending through said second steering wire lumen, and a looped segment connecting said first and second legs, free ends of said first and second legs being coupled to said steering actuator;
      (ii) a first wear-resistant sleeve within said first steering wire lumen adjacent said looped segment of said steering wire, said first wear-resistant sleeve defining an opening therethrough for passage of said first leg of steering wire; and
      (iii) a second wear-resistant sleeve within said second steering wire lumen adjacent said looped segment of said steering wire, said second wear-resistant sleeve defining an opening therethrough for passage of said second leg of steering wire;
      wherein said looped segment of said steering wire comprises a coined portion having an expanded outer dimension larger than said openings through said first and second wear-resistant sleeves;
   (d) at least one inlet housing mounted to said catheter body housing, one said inlet housing corresponding to each of said at least one access lumens; and
   (e) at least one access conduit, each access conduit coupling an inlet housing to the corresponding access lumen.

3. The steerable catheter of claim 2, wherein said segmented catheter shaft comprises:
   (a) a first shaft segment having a first stiffness, said first shaft segment comprising a rear distal end connected to said catheter body housing, and a front distal end opposite said rear distal end;
   (b) a tip segment having a second stiffness less than said first stiffness, said tip segment comprising a first end fused to the front distal end of said first shaft segment, and a second end opposite said first end;
   (c) an end segment having a third stiffness greater than said second stiffness, said end segment comprising a first end fused to the second end of said tip segment, and a second end opposite said first end; and
   (d) a cover segment overlying at least a portion of the second end of said end segment;
   wherein said looped segment of steering wire is encapsulated between said second end of said tip segment and said cover segment.

4. The steerable catheter of claim 2, wherein said inlet housing comprises a unitary body portion comprising a mounting flange attached to said catheter body housing, and a flush port rigidly fixed in position relative to said mounting flange.

5. The tip assembly of claim 1, wherein said coined portion is formed by crimping to deform the wire.

6. The tip assembly of claim 1, wherein said expanded outer dimension lies in a plane intersecting said first and second legs of said steering wire.

7. The tip assembly of claim 1, wherein the entire looped segment of said steering wire is coined to have an expanded outer dimension larger than said openings through said first and second wear-resistant sleeves.

8. The tip assembly of claim 1, wherein the coined portion has a reduced thickness in a dimension generally perpendicular to said expanded outer dimension.

9. The steerable catheter of claim 2, wherein said coined portion is formed by crimping to deform the wire.

10. The steerable catheter of claim 2, wherein said expanded outer dimension lies in a plane intersecting said first and second legs of said steering wire.

11. The steerable catheter of claim 2, wherein the entire looped segment of said steering wire is coined to have an expanded outer dimension larger than said openings through said first and second wear-resistant sleeves.

12. The steerable catheter of claim 2, wherein the coined portion of the steering wire has a reduced thickness in a dimension generally perpendicular to said expanded outer dimension.

13. A steerable catheter comprising:
    a body comprising a steering actuator;
    a catheter shaft defining first and second steering wire lumens extending therethrough, said catheter shaft having a first end attached to said body and a second end opposite said first end;

a first wear-resistant sleeve within said first steering wire lumen adjacent the second end of said catheter shaft, said first wear-resistant sleeve defining a passage therethrough;

a second wear-resistant sleeve within said second steering wire lumen adjacent the second end of said catheter shaft, said second wear-resistant sleeve defining a passage therethrough; and a length of steering wire comprising:
- a first leg extending through the passage in said first wear-resistant sleeve and through said first steering wire lumen, and terminating in a first end connected to said steering actuator;
- a second leg extending through the passage in said second wear-resistant sleeve and through said second steering wire lumen, and terminating in a second end connected to said steering actuator; and
- a looped segment connecting said first and second legs, wherein said looped segment comprises a coined portion having an expanded outer dimension larger than said passages through said first and second wear-resistant sleeves.

14. The steerable catheter of claim 13, wherein said coined portion is formed by crimping to deform the steering wire.

15. The steerable catheter of claim 13, wherein said expanded outer dimension lies in a plane intersecting said first and second legs of said steering wire.

16. The steerable catheter of claim 13, wherein the entire looped segment of said steering wire is coined to have an expanded outer dimension larger than said openings through said first and second wear-resistant sleeves.

17. The steerable catheter of claim 13, wherein the coined portion has a reduced thickness in a dimension generally perpendicular to said expanded outer dimension.

* * * * *